United States Patent
Kuramoto et al.

(10) Patent No.: US 10,905,644 B2
(45) Date of Patent: Feb. 2, 2021

(54) METHOD FOR TREATING HAIR

(71) Applicant: KAO CORPORATION, Tokyo (JP)

(72) Inventors: Kyoko Kuramoto, Shinagawa-ku (JP);
Shinobu Nagase, Nakano-ku (JP);
Takeshi Iizaki, Saitama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/648,761

(22) PCT Filed: Sep. 20, 2018

(86) PCT No.: PCT/JP2018/034759
§ 371 (c)(1),
(2) Date: Mar. 19, 2020

(87) PCT Pub. No.: WO2019/059264
PCT Pub. Date: Mar. 28, 2019

(65) Prior Publication Data
US 2020/0268630 A1 Aug. 27, 2020

(30) Foreign Application Priority Data

Sep. 20, 2017 (JP) .................. 2017-180756
Mar. 1, 2018 (JP) .................. 2018-036713

(51) Int. Cl.
*A61Q 5/10* (2006.01)
*A61K 8/49* (2006.01)

(52) U.S. Cl.
CPC .......... *A61K 8/49* (2013.01); *A61K 8/494* (2013.01); *A61K 8/4926* (2013.01); *A61K 8/4946* (2013.01); *A61Q 5/10* (2013.01)

(58) Field of Classification Search
CPC ...... A61Q 5/065; A61K 8/4926; A61K 8/494; A61K 8/49; A61K 8/4946;
(Continued)

(56) References Cited

U.S. PATENT DOCUMENTS 10,470,990 B2 * 11/2019 Saimiya .................. A61K 8/817
10,772,815 B2 * 9/2020 Saimiya .................... A61K 8/19
(Continued)

FOREIGN PATENT DOCUMENTS

| EP | 2 574 331 A2 | 4/2013 |
| EP | 3 153 154 A1 | 4/2017 |

(Continued)

OTHER PUBLICATIONS

International Search Report dated Dec. 13, 2018 in PCT/JP2018/034759 filed Sep. 29, 2018.
(Continued)

Primary Examiner — Eisa B Elhilo
(74) Attorney, Agent, or Firm — Oblon, McClelland, Maier & Neustadt, L.L.P.

(57) ABSTRACT

A method for treating hair, in which using as a boundary a depth X % in a range of 5% to 80% from the surface of hair toward the center along the long diameter axis extending through the center of the cross-section of hair, hair is divided into an A layer (a portion of a continuous color from the surface of hair to the depth X %) and a B layer (a portion including the center and having a continuous color different from the A layer, in which the depth from the surface of hair exceeds X %) and at least one value of ΔE*, Δh and ΔC* between the color of the A layer and the color of the B layer is adjusted to 3 or more to change the hue and the color tone of hair appearance depending on viewing angle of the hair. A method for dyeing hair, having Step (I) of dyeing hair with a two-part permanent hair dye agent, and Step (II) of dyeing hair with a hair dye agent comprising a dye selected from (A-1) to (A-8).

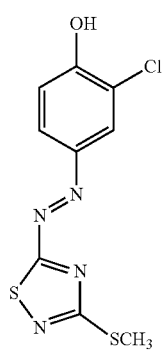

(A-1)

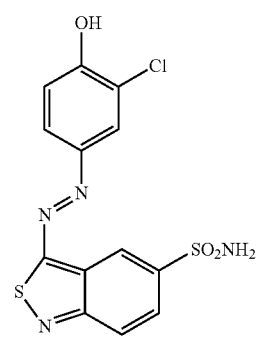

(A-2)

(Continued)

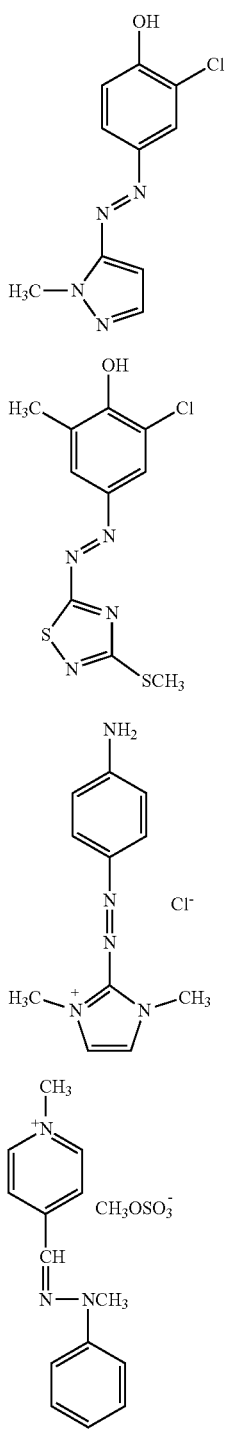

(A-3)
(A-4)
(A-5)
(A-6)

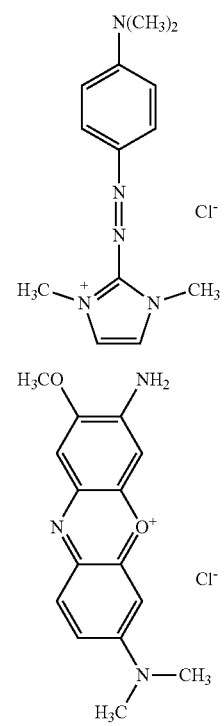

(A-7)
(A-8)

3 Claims, No Drawings

(58) Field of Classification Search
CPC ...... A61K 2800/4324; A61K 2800/884; A61K 8/4953; A61K 2800/5426; A61K 2800/4322
USPC .................................................. 8/405, 437
See application file for complete search history.

(56) References Cited

U.S. PATENT DOCUMENTS

| | | | |
|---|---|---|---|
| 2004/0019982 A1* | 2/2004 | Pratt | A61K 8/492 8/405 |
| 2007/0215169 A1 | 9/2007 | Daneshvar | |
| 2013/0061866 A1 | 3/2013 | Klingelmeyer et al. | |
| 2017/0196791 A1 | 7/2017 | Nojiri | |

FOREIGN PATENT DOCUMENTS

| | | |
|---|---|---|
| JP | 6-271435 A | 9/1994 |
| JP | 2003-342139 A | 12/2003 |
| JP | 2019-55944 A | 4/2019 |
| JP | 2019-55945 A | 4/2019 |
| JP | 2019-55946 A | 4/2019 |

(56) References Cited

FOREIGN PATENT DOCUMENTS

| JP | 2019-55947 A | 4/2019 |
| JP | 2019-151615 A | 9/2019 |
| WO | WO 2015/186816 A1 | 12/2015 |

OTHER PUBLICATIONS

Simone Aparecida da Franca, et al., "Types of Hair Dye and Their Mechanisms of Action," Cosmetics, doi:10.3390/cosmetics2020110, vol. 2, XP055530200, 2015, pp. 110-126.

* cited by examiner

METHOD FOR TREATING HAIR

TECHNICAL FIELD

The present invention relates to a method for treating hair, in which the hue and the color tone of hair appearance are changed depending on viewing angle of the hair.

BACKGROUND ART

Hair dye agents can be classified by dyes used or the presence or absence of the action of bleaching on melanin. Typical examples of hair dye agents include a two-agent type permanent hair dye agent containing a first agent containing an alkaline agent and an oxidation dye intermediate and a second agent containing an oxidizing agent, and a one-agent type semipermanent hair dye agent containing an organic acid or an alkaline agent and at least one of direct dyes such as an acidic dye, a basic dye and a nitro dye.

Permanent hair dye agents have excellent aspects of penetrating the deep part of hair, uniformly dyeing from the center of hair to the surface, and maintaining a hair dyeing effect because of resistance to color fading; however, there is a problem that a color tone provided by an oxidation dye is not so vivid. Direct dyes meanwhile are inferior in fastness due to low penetration into hair; however, some direct dyes, for example nitro dyes, can give a vivid color (see e.g., PTL 1).

(PTL 1) JP Hei 6-271435 A

SUMMARY OF INVENTION

The present invention provides a method for treating hair, in which hair is divided into the following A layer and B layer using as a boundary a depth X % in a depth range of 5% or more and 80% or less from the surface of hair toward the center along the long diameter axis extending through the center of the cross-section of hair, and at least one value of $\Delta E^*$, $\Delta h$ and $\Delta C^*$ between the color of the A layer and the color of the B layer is adjusted to 3 or more to provide visual changes in the hue and the color tone of hair appearance depending on viewing angle of the hair:

A layer: a portion of a continuous color from the surface of hair to the depth X %, and B layer: a portion including the center and having a continuous color different from the A layer, in which the depth from the surface of hair exceeds X %.

The present invention further provides a method for dyeing hair, having the following steps (I) and (II):

Step (I): dyeing or bleaching hair by applying to hair a mixture obtained by mixing a first agent comprising an alkaline agent and a second agent comprising an oxidizing agent, and Step (II): after the step (I), dyeing hair by applying to hair a hair dye agent comprising one or more dyes (A) selected from the group consisting of the following (A-1) to (A-8).

[Chem. 1]

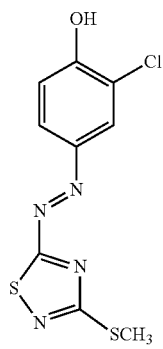
(A-1)

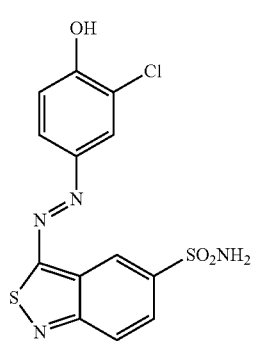
(A-2)

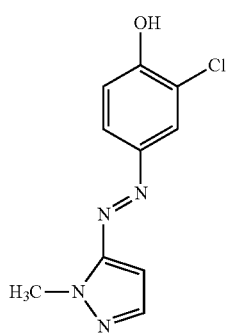
(A-3)

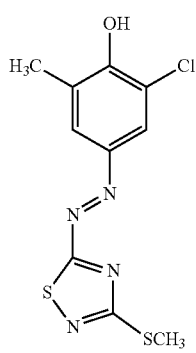
(A-4)

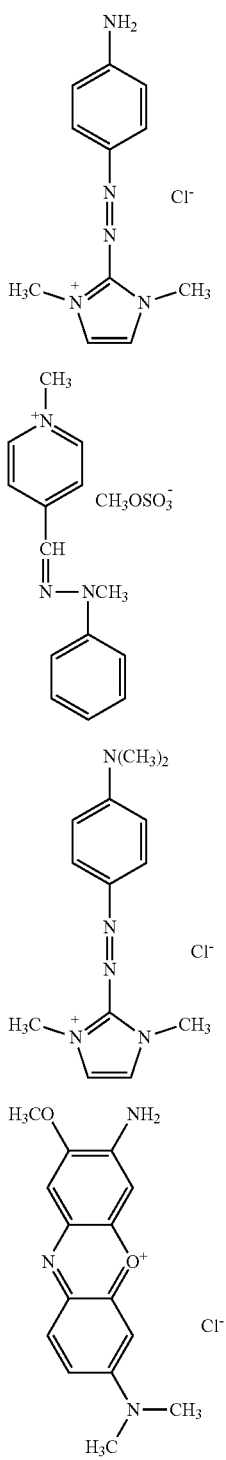

(A-5)
(A-6)
(A-7)
(A-8)

DETAILED DESCRIPTION OF THE INVENTION

To the above problem in a permanent hair dye agent, there is also an attempt to simultaneously use a hair dye agent containing an oxidation dye intermediate and a hair dye agent containing a direct dye to provide the advantages of the two; however, few direct dyes are stable to alkaline agents and oxidizing agents, and it is difficult to exert the effects of direct dyes. Furthermore, the technique for combining an oxidation dye and a direct dye as described above is nothing but a technique to improve the finish of dyeing, which technique aims to dye hair in more vivid color with a permanent hair dye agent. Recent consumers meanwhile have tended to desire a special finish with beauty and an impact.

Therefore, the present invention relates to a method for treating hair, in which a special finish with beauty and an impact desired by consumers is obtained, and moreover a method for dyeing hair, which method uses an oxidation dye and a specific direct dye at the same time and utilizes a difference in penetration into hair between both dyes, and provides a hair dyeing effect which has not been seen until now.

As a result of investigations on a method for treating hair which provides a finish which has not been seen until now, the present inventors found that by dyeing the peripheral part and the center part of hair with different colors, the hue and the color tone of hair appearance changed depending on viewing angle of the hair and the hue and the color tone changed also depending on hair movement. As a result of further investigations, the range of the boundary between different colors to obtain such effect in a region from the periphery of hair to the center part was found, thereby completing the present invention.

The present invention provides the effect of increasing changes in the hue and the color tone of hair appearance depending on viewing angle of the hair, and the shape and movement of hair look outstanding.

The method for treating hair of the present invention is characterized in that hair is divided into the following A layer and B layer using as a boundary a depth X % in a depth range of 5% or more and 80% or less from the surface of hair toward the center along the long diameter axis extending through the center of the cross-section of hair, and colors of these A layer and B layer are changed:

A layer: a portion of a continuous color from the surface of hair to the depth X %, and B layer: a portion including the center and having a continuous color different from the A layer, in which the depth from the surface of hair exceeds X %.

The depth X % is preferably 7% or more, more preferably 10% or more, further preferably 15% or more, further preferably 17% or more, and further preferably 20% or more from the viewpoint of the effect of increasing changes in the hue and the color tone of hair appearance depending on viewing angle of the hair, and preferably 75% or less, more preferably 65% or less, further preferably 60% or less, further preferably 55% or less, and further preferably 50% or less.

(Method for Measuring Depth X)

The depth X % in the present invention means the ratio of the thickness of an A layer from the surface of hair toward the central part, and is also a boundary surface between the A layer and B layer. A hair is sliced at a thickness of about 20 μm, and a cross-section of the hair is observed with an optical microscope or laser microscope. After photographing, the long diameter of the hair and the total length of an A layer in the long diameter direction are measured, and the depth X % represents the proportion of the latter to the former by percentage. When the outlines of hue and the color tone are clear, the outline is determined as the boundary surface between an A layer and a B layer, and when the outlines of hue and color tone are unclear, a midpoint in a gradation portion is determined as the boundary surface. As a method for accurately verifying such midpoint, there is a means in which changes in L*a*b values or RGB values on a microscope image are monitored along the long diameter axis of hair using an image analysis software (Image J manufactured by National Institutes of Health), and in a position in which any value changes most greatly, the midpoint between the starting point and ending point of the change is determined as the boundary surface between an A layer and a B layer (with the proviso that when there is medulla tissue having a cavity in the central part of hair and thus L*a*b* changes most greatly on the boundary between the medulla and cortex, except for such position, a position in which L*a*b* changes most greatly is used to measure a depth X). In a hair having medulla tissue, the medulla part is also considered to constitute the B layer.

(Method for Measuring Colors of A Layer and B Layer)

In the present invention, the colors of an A layer and a B layer can be verified by slicing a hair at a thickness of about 20 µm and observing a cross-section with an optical microscope or a laser microscope. However, in the present invention, in order to verify the colors of an A layer and a B layer of hair, a method in which the color of the surface of hair after hair dyeing is directly measured by a color-difference meter can be adopted. That is, the color of an A layer of hair can be verified by directly measuring the surface of hair having a two-layer structure, and as the color of a B layer, the surface of hair without an A layer is directly measured. The hair without an A layer refers to, for example when two layers of the present invention are dyed with different dyes, hair dyed only with a dye used to dye a B layer. As a method for measuring the surface of hair, it is preferable that each average value of L*, a*, b*, C* and h values obtained by measuring different 6 points on the surface of hair (each one point in the central part on the front and back in each region obtained by dividing a hair tress into 3 portions in the length direction) using a chroma meter CR-400 manufactured by KONICA MINOLTA, Inc. be considered as the color of the surface of hair.

(Difference in Colors Between A Layer and B Layer)

The degree of difference in colors between an A layer and a B layer in the present invention is set such that at least one value of color difference ΔE*, hue difference Δh and chroma difference ΔC* between the A layer and B layer measured by the meter will be 3 or more. The ΔE* is preferably 3 or more, more preferably 5 or more, further preferably 8 or more, further preferably 10 or more, further preferably 15 or more, further preferably 20 or more, further preferably 25 or more, and further preferably 30 or more from the viewpoint of increasing changes in the hue and the color tone of hair appearance depending on viewing angle of the hair. In addition, the Δh is preferably 3 or more, more preferably 5 or more, further preferably 8 or more, further preferably 10 or more, further preferably 15 or more, further preferably 20 or more, further preferably 25 or more, and further preferably 30 or more from the same viewpoint. Furthermore, the ΔC* is preferably 3 or more, more preferably 5 or more, further preferably 8 or more, further preferably 10 or more, further preferably 15 or more, further preferably 20 or more, further preferably 25 or more, and further preferably 30 or more from the same viewpoint.

(Changes in Hue and Color Tone of Hair Appearance Depending on Viewing Angle of the Hair)

The visual effect of changes in the hue and the color tone of hair appearance depending on viewing angle of the hair in the present invention can be identified as follows. Specifically, the effect can be identified by differences of $\Delta E^*_0$, $\Delta h_0$ and $\Delta C^*_0$ values between two points with the highest contrast on the surface of hair having only a color in a B layer without an A layer, and $\Delta E^*_1$, $\Delta h_1$ and $\Delta C^*_1$ values between two points with the highest contrast on the surface of hair having an A layer and a B layer, where the angles of a line connecting a light source and hair, and a line connecting hair and observer's eyes, and/or the angles of the surface of hair are changed. The "contrast" used herein means that at least one of brightness, hue and chroma is greatly different except for a highlighted region in which light from a light source directly reflects. The $\Delta E^*_1 - \Delta E^*_0$ is preferably 3 or more, more preferably 3.3 or more, further preferably 5 or more, further preferably 8 or more, further preferably 10 or more, further preferably 15 or more, further preferably 20 or more, further preferably 25 or more, and further preferably 30 or more from the viewpoint of increasing changes in the hue and the color tone of hair appearance depending on viewing angle of the hair. In addition, the $\Delta h_1 - \Delta h_0$ is preferably 3 or more, more preferably 3.3 or more, further preferably 5 or more, further preferably 8 or more, further preferably 10 or more, further preferably 15 or more, further preferably 20 or more, further preferably 25 or more, and further preferably 30 or more from the same viewpoint. Furthermore, the $\Delta C^*_1 - \Delta C^*_0$ is preferably 3 or more, more preferably 3.3 or more, further preferably 5 or more, further preferably 8 or more, further preferably 10 or more, further preferably 15 or more, further preferably 20 or more, further preferably 25 or more, and further preferably 30 or more from the same viewpoint.

$\Delta E^*_0$, $\Delta h_0$ and $\Delta C^*_0$, and $\Delta E_1$, $\Delta h_1$ and $\Delta C^*_1$ can be measured as follows.

A hair tress to be measured is fixed along the curve of, for example, a cylindrical stand to provide a certain curvature. This hair tress is put under a light source, and photographs are taken at a fixed distance of about 1 m from the hair tress at various angles in the circumferential direction and axis direction of the cylindrical stand. At this time, the brightness of the light source can be variously changed, and the curvature radius of the cylindrical stand can be also variously changed. The taken images thereof are printed out, and it is preferable that colors be measured on the images. At this time, the color difference (ΔE*), hue difference (Δh) and chroma difference (ΔC*) between two strip-shaped regions in which e.g. brightness, hue and chroma are most different, which regions are near a highlighted region (a strip-shaped region which is generated by mirror reflection of light from a light source and appears bright), are measured by a color-difference meter to identify the greatest ΔE*, Δh and ΔC*. The "two strip-shaped regions in which e.g. brightness, hue and chroma are different" can appear on both sides of the highlighted region, or can appear next to each other on one side. In addition, when two highlighted regions appear separately, the two regions in which e.g. brightness, hue, and chroma are most different can appear between two highlighted regions. The decision which case appears is visually made.

When hair without an A layer is used as a reference for hair having an A layer and a B layer with different colors (hair entirely dyed only with an agent used to dye a B layer for hair having an A layer and a B layer separately dyed, and hair before hair dyeing for hair in which a B layer is not dyed and only an A layer is dyed), and at least one difference of the above color difference ($\Delta E^*$), hue difference ($\Delta h$) and chroma difference ($\Delta C^*$), i.e. at least one of A ($\Delta E^*$)=$\Delta E^*$ (target hair)−$\Delta E^*$ (reference), $\Delta$ ($\Delta h$)=$\Delta h$ (target hair)−$\Delta h$ (reference), and $\Delta$ ($\Delta C^*$)=$\Delta C^*$ (target hair)−$\Delta C^*$ (reference) is 3 or more, the "effect of showing changes in hue and color tone depending on viewing angle of the hair" is expressed. A target hair and its reference are put on the cylindrical stand next to each other, and photographs thereof are taken. However, angles at which the target hair and its reference each have the most different $\Delta E^*$, $\Delta h$ or $\Delta C^*$ are not necessarily the same.

On the assumption that a target hair and its reference are certainly measured and compared on the same conditions of, for example, the type and intensity of light source and the curvature of a hair tress, the conditions can be adjusted such that proper evaluation results will be obtained.

The color of a B layer can be the color of hair itself, or can be the color of bleached hair, and is preferably a color dyed with a dye which penetrate the center of hair to uniformly dye from the center to surface, and more preferably a color dyed with an oxidation dye intermediate from the viewpoint of the degree of the effect of increasing changes in the hue and the color tone of hair appearance depending on viewing angle of the hair. An oxidation dye intermediate used for hair dyeing with an oxidation dye can contain a precursor and a coupler which are commonly used for a hair dye agent.

Examples of precursors include p-phenylenediamine, toluene-2,5-diamine, o-chloro-p-phenylenediamine, N-phenyl-p-phenylenediamine, N,N-bis(hydroxyethyl)-p-phenylenediamine, 3-methyl-4-aminophenol, 2-hydroxyethyl-p-phenylene, p-aminophenol, p-methylaminophenoldiamine, p-aminophenol, p-methylaminophenol, 4-amino-m-cresol, o-aminophenol, 2-methoxymethyl-p-phenylenediamine, hydroxyethoxyaminopyrazolopyridine, 2,3-diaminodihydroxypyrazolopyrazolone, N-methoxyethyl-p-phenylenediamine, 2,6-dimethyl-p-phenylenediamine, 4,4'-diaminodiphenylamine, 1,3-bis(N-(2-hydroxyethyl)-N-(4-aminophenyl)amino)-2-propanol, PEG-3,2,2'-p-phenylenediamine, 2-aminomethyl-4-aminophenol, 2-(2-hydroxyethylaminomethyl)-4-aminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraaminopyrimidine, 2,5,6-triamino-4-hydroxypyrimidine, 4,5-diamino-1-(4'-chlorobenzyl)pyrazole, and salts thereof.

Examples of couplers include resorcin, 2-methylresorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, 2-amino-3-hydroxypyridine, p-aminophenol, o-aminophenol, 2-amino-4-(2-hydroxyethylamino) anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy) propane, 2-methyl-5-aminophenol, 2,4-dichloro-3-aminophenol, 2-chloro-3-amino-6-methylphenol, 2-methyl-4-chloro-5-aminophenol, N-cyclopentyl-m-aminophenol, 2-methyl-4-methoxy-5-(2-hydroxyethylamino)phenol, 2-methyl-4-fluoro-5-aminophenol, 4-chlororesorcin, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, and salts thereof.

The color of an A layer is preferably one obtained by hair dyeing with a dye, and more preferably a color dyed with a direct dye, which is a dye not penetrating the center of hair and dyeing the vicinity of the surface, or a color dyed with this direct dye after bleaching, or a color dyed with this direct dye after dyeing from the center to surface with a dye used to dye the above-described B layer (e.g. an oxidation dye intermediate). Among these, a color dyed using a dye containing one or more dyes (A) selected from the group consisting of the following (A-1) to (A-8) as a direct dye is further preferable from the viewpoint of increasing changes in the hue and the color tone of hair appearance depending on viewing angle of the hair. The dye (A) is more preferably one or more selected from the group consisting of the following (A-1) to (A-4), and further preferably one or more selected from the group consisting of the following (A-1) to (A-3) from the same viewpoint.

[Chem. 2]

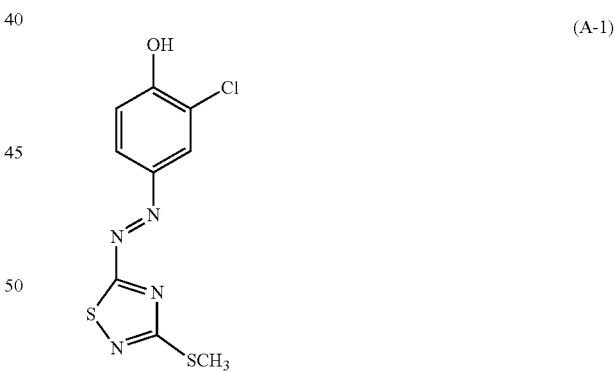

(A-1)

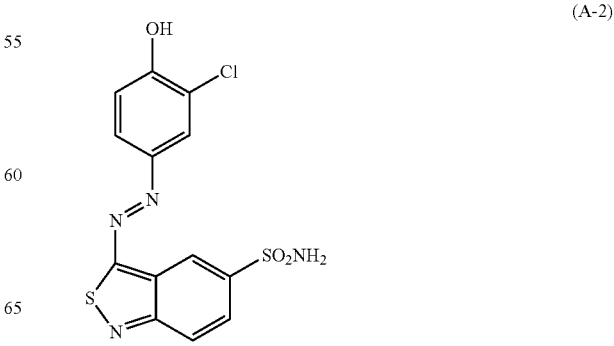

(A-2)

-continued (A-3) 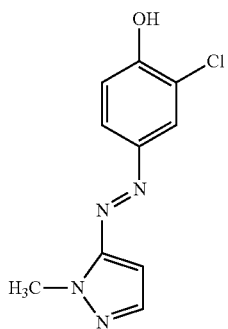

(A-4) 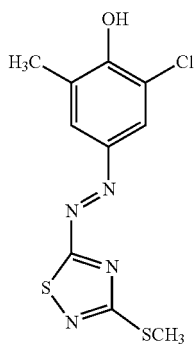

(A-5) 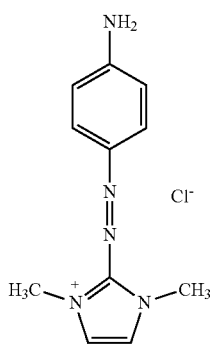

(A-6) 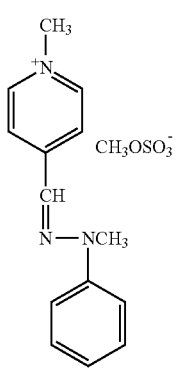

(A-7) 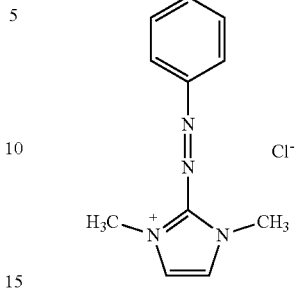

(A-8) 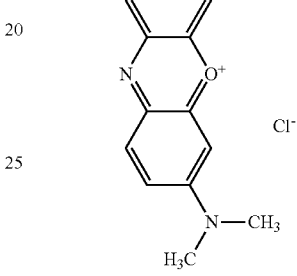

<Method for Dyeing Hair>

Examples of preferable aspects for the method for treating hair of the present invention include a method for dyeing hair, having the following steps (I) and (II):

Step (I): dyeing or bleaching hair by applying to hair a mixture obtained by mixing a first agent containing an alkaline agent and a second agent containing an oxidizing agent, and Step (II): after the step (I), dyeing hair by applying to hair a hair dye agent containing one or more dyes (A) selected from the group consisting of the (A-1) to (A-8).

(Step (I))

Step (I) is a step of applying a mixture obtained by mixing a first agent and a second agent to hair, and can be carried out in the same manner as a known step of dyeing or bleaching using a two-part or three-part permanent hair dye agent or hair bleaching agent.

Examples of alkaline agents contained in a first agent used in the step (I) include ammonia and salts thereof; alkali metal hydroxides such as sodium hydroxide and potassium hydroxide; alkanolamines such as monoethanolamine, isopropanolamine, 2-amino-2-methylpropanol and 2-aminobutanol and salts thereof; alkanediamines such as 1,3-propanediamine and salts thereof; carbonates such as sodium carbonate, potassium carbonate and guanidine carbonate; and hydrogen carbonates such as sodium hydrogen carbonate and potassium hydrogen carbonate.

The alkaline agents can be used singly or in combination of two or more. The content of alkaline agent in a mixed solution of a first agent and a second agent is preferably 0.01 mass % or more, more preferably 0.05 mass % or more, further preferably 0.1 mass % or more, and further preferably 0.2 mass % or more from the viewpoint of sufficiently swelling hair to obtain the effect of dyeing or bleaching hair, and preferably 20 mass % or less, more preferably 10 mass % or less, further preferably 5 mass % or less, and further preferably 4 mass % or less from the viewpoint of suppressing hair damage and skin stimulation.

When the step (I) is a step of dyeing hair using a permanent hair dye agent, a first agent further contains an oxidation dye intermediate. When the step (I) is a step of bleaching using a hair bleaching agent, a first agent does not contain a dye. As the oxidation dye intermediate contained in a first agent used in the step (I), the precursor and coupler mentioned above can be used.

The precursors can be used singly or in combination of two or more. The content of precursor in a first agent is preferably 0.003 mass % or more, more preferably 0.005 mass % or more, and further preferably 0.01 mass % or more from the viewpoint of imparting sufficient hair dyeability, and preferably 10 mass % or less, more preferably 8 mass % or less, and further preferably 5 mass % or less from the viewpoint of the stability of the agent.

The couplers can be used singly or in combination of two or more. The content of coupler in a first agent is preferably 0.003 mass % or more, more preferably 0.005 mass % or more, and further preferably 0.01 mass % or more from the viewpoint of imparting sufficient hair dyeability and of the stability of the agent, and preferably 10 mass % or less, more preferably 8 mass % or less, and further preferably 5 mass % or less from the viewpoint of the stability of the agent.

Two or more precursors or couplers, respectively, can be used in combination from the viewpoint of imparting sufficient hair dyeability and of the stability of the agent.

Examples of oxidizing agents contained in a second agent used in the step (I) include hydrogen peroxide; persulfates such as ammonium persulfate, potassium persulfate and sodium persulfate; perborates such as sodium perborate; percarbonates such as sodium percarbonate; bromates such as sodium bromate and potassium bromate. Among these, hydrogen peroxide is particularly preferable in terms of bleachability on hair, dye stability and dye effectiveness.

The oxidizing agents can be used singly or in combination of two or more. The content of oxidizing agent in a mixed solution is preferably 0.25 mass % or more, more preferably 0.5 mass % or more, and further preferably 1.0 mass % or more from the viewpoint of bleachability on hair, and preferably 10 mass % or less, more preferably 7.5 mass % or less, and further preferably 6.5 mass % or less from the viewpoint of suppressing skin stimulation and hair damage.
(pH)

The pH of a mixed solution is preferably 7.5 or higher, more preferably 8.0 or higher, further preferably 8.5 or higher, and further preferably 9.0 or higher from the viewpoint of imparting sufficient hair dyeability or bleachability, and preferably 12.0 or lower, more preferably 11.5 or lower, and further preferably 11.0 or lower from the viewpoint of suppressing skin stimulation. In addition, it is preferable that the pH of a first agent be 8 or higher and 12 or lower, and the pH of a second agent be 2 or higher and 5 or lower. In addition, a third agent containing an oxidizing aid can be further mixed in the step (I). In the present invention, the pH of first to third agents and a mixed solution thereof means a value at 25° C. when diluted by 10 times by mass with water using a pH meter (F-51 manufactured by Horiba, Ltd.)

Examples of pH adjustors to adjust a composition to the above pH include inorganic acids such as hydrochloric acid and phosphoric acid, organic acids such as citric acid, glycolic acid and lactic acid, hydrochlorides such as ammonium chloride and monoethanolamine hydrochloride, and phosphates such as monopotassium dihydrogen phosphate and disodium monohydrogen phosphate along with the alkaline agents.

To a first agent and a second agent used in the step (I), other components which are commonly used as cosmetic materials along with water as a medium can be further added as long as a stable form of liquid and function as a hair dye agent or a hair bleaching agent are not impaired. Examples of objects to blend such optional components can include viscosity control, penetration enhancement, pearlization, antisepsis, metal blockade, stabilization, antioxidation, ultraviolet absorption, moisture retention, product coloration and perfuming, and specific examples of optional components include surfactants, thickening agents, animal and plant fat and oil, higher fatty acids, hydrolyzed proteins, protein derivatives, amino acids, botanical extracts, vitamins, pigments and perfumes.

Examples of hair dye compositions or hair bleaching agents used in the step (I) include a two-part type comprising a first agent containing an alkaline agent or an alkaline agent and an oxidation dye intermediate and a second agent containing an oxidizing agent, and a three-part type comprising the above first agent and second agent, and moreover a third agent containing, for example, a persulfate as an oxidizing agent (oxidizing aid). Each agent can be in any form of, for example, liquid, gel, sherbet, slurry, emulsion, cream, ointment, solid pasty, paste, solid and powder, and can be also in a form of aerosol, which extrudes the above by gas pressure. A combination of forms of a first agent, a second agent and a third agent can be any combination of the above forms. Any one of the agents is desirably in a form of liquid, gel, emulsion or cream, more preferably in a form of liquid or emulsion, and further preferably in a form of liquid from the viewpoint of miscibility and applying properties.

When a mixed solution is applied to hair, a bath ratio, i.e. the ratio of the mass of mixed solution to be applied to the mass of hair [(the mass of mixed solution to be applied)/(the mass of hair)], time for and temperature at which a mixed solution is left to stand from application to hair to washing hair have a large effect on the finish.

The content of precursor in a mixed solution obtained after mixing a first agent and a second agent is preferably 0.001 mass % or more, more preferably 0.002 mass % or more, and further preferably 0.004 mass % or more from the viewpoint of imparting sufficient hair dyeability, and preferably 8 mass % or less, more preferably 6 mass % or less, and further preferably 4 mass % or less. In addition, the content of coupler in a mixed solution is preferably 0.001 mass % or more, more preferably 0.002 mass % or more, and further preferably 0.004 mass % or more from the viewpoint of imparting sufficient hair dyeability and of the stability of agents, and preferably 8 mass % or less, more preferably 6 mass % or less, and further preferably 4 mass % or less.

The bath ratio is preferably 0.2 or more, more preferably 0.4 or more, and further preferably 0.6 or more from the viewpoint of improving hair dyeability or bleachability, and preventing color unevenness, and preferably 2 or less, more preferably 1.75 or less, and further preferably 1.5 or less from the viewpoint of economical efficiency and reducing a risk of dripping.

The time for which a mixed solution is left to stand from application to hair to washing hair is preferably a minute or longer, more preferably 5 minutes or longer, and further preferably 10 minutes or longer from the viewpoint of improving hair dyeability, and preferably 60 minutes or shorter, more preferably 45 minutes or shorter, and further preferably 40 minutes or shorter from the viewpoint of suppressing skin stimulation.

The temperature at which a mixed solution is applied to hair and left to stand is preferably 5° C. or higher, more preferably 10° C. or higher, and further preferably 20° C. or higher from the viewpoint of improving hair dyeability or bleachability, and preferably 60° C. or lower, more preferably 50° C. or lower, and further preferably 40° C. or lower from the viewpoint of suppressing skin stimulation.

After the step (I), hair can be rinsed and/or washed. For rinsing, optional aqueous media known in the art, preferably water, more preferably tap water can be used, and for washing, optional washing compositions known in the art, preferably a shampoo composition can be used. The root portion, tip portion and portion between them of hair can be simultaneously or separately rinsed and washed. In addition, after or before the above rinsing or washing, or instead of rinsing or washing, an optional conditioning composition known in the art can be applied to hair.

After the step (I) and the above optional rinsing and/or washing, hair can be optionally dried. Drying tools e.g. towel or an electric drying tool such as a fan dryer can be used to dry hair, and hair can be partially or completely dried.

(Step (II))

Step (II) is a step of dyeing hair by applying to hair a hair dye agent containing one or more dyes (A) selected from the group consisting of the (A-1) to (A-8) after the step (I). As the dyes (A), (A-1) to (A-4) are preferable and (A-1) to (A-3) are more preferable from the viewpoint of the degree of the effect of increasing changes in the hue and the color tone of hair depending on viewing angle of the hair.

The content of dye (A) in a hair dye agent used in the step (II) (for a two-part hair dye agent, in a mixed solution obtained after mixing a first agent and a second agent) is preferably 0.02 mass % or more, more preferably 0.05 mass % or more, further preferably 0.08 mass % or more, and further preferably 0.1 mass % or more from the viewpoint of imparting sufficient hair dyeability, and preferably 5 mass % or less, more preferably 2 mass % or less, further preferably 1.0 mass % or less, and further preferably 0.5 mass % or less from the viewpoint of economical efficiency.

To a hair dye agent used in the step (II), other components which are commonly used as cosmetic materials along with water as a medium can be further added as long as a stable form of liquid and function as a hair dye agent are not impaired. Examples of such optional components can include viscosity modifiers, penetration enhancers, pearly pigments, antiseptic agents, sequestering agents, stabilizing agents, antioxidants, ultraviolet absorbing agents, moisturizing agents, and odor-control agents, and specific examples of optional components include surfactants, thickening agents, animal and plant fat and oil, higher fatty acids, hydrolyzed proteins, protein derivatives, amino acids, botanical extracts, vitamins, and perfumes.

Examples of hair dye agents used in the step (II) include a one-part type comprising a single composition, a two-part hair dye agent comprising a first agent and a second agent containing a general cosmetic material such as an oxidizing agent. Each agent can be in any form of, for example, liquid, gel, sherbet, slurry, emulsion, cream, ointment, solid pasty, paste, solid and powder, and can be also in a form of aerosol, which extrudes the above by gas pressure. In addition, a combination of forms of a first agent and a second agent may include any combination of the above forms. Any one of the agents is desirably in a form of liquid, gel, emulsion or cream, more preferably in a form of liquid or emulsion, and further preferably in a form of liquid from the viewpoint of miscibility and applying properties.

As the mixing ratio of a first agent and a second agent, an optional mixing ratio can be selected such that a sufficient concentration of dye and an oxidizing agent are contained from the viewpoint of hair dyeability and such that a proper mixing viscosity is obtained from the viewpoint of applying properties. The mixing mass ratio of a first agent and a second agent (second agent/first agent) is preferably from 0.2 to 5, more preferably from 0.3 to 3, and further preferably from 0.5 to 2. For the above mixing, optional suitable mixing and/or applying tools known in the art can be used. Preferable examples thereof include mixing with a brush in a container in a form of bowl, and mixing by penetration in a container integrated with an applicator.

When a hair dye agent (for a two-part type, a mixed solution, the same applies hereinafter) is applied to hair, a bath ratio, i.e. the ratio of the mass of hair dye agent to be applied to the mass of hair [(the mass of hair dye agent to be applied)/(the mass of hair)], time for and temperature at which a mixed solution is left to stand from application to hair to washing hair have a large effect on the finish.

The bath ratio is preferably 0.2 or more, more preferably 0.4 or more, and further preferably 0.6 or more from the viewpoint of improving hair dyeability, and preventing color unevenness, and preferably 2 or less, more preferably 1.75 or less, and further preferably 1.5 or less from the viewpoint of economical efficiency and reducing a risk of dripping.

The time for which a hair dye agent is left to stand from application to hair to washing hair is preferably a minute or longer, more preferably 5 minutes or longer, and further preferably 10 minutes or longer from the viewpoint of improving hair dyeability, and increasing changes in the hue and the color tone of hair appearance depending on viewing angle of the hair, and preferably 60 minutes or shorter, more preferably 50 minutes or shorter, further preferably 45 minutes or shorter, and further preferably 40 minutes or shorter from the viewpoint of suppressing skin stimulation.

The temperature at which a mixed solution is applied to hair and left to stand is preferably 5° C. or higher, more preferably 10° C. or higher, and further preferably 20° C. or higher from the viewpoint of improving hair dyeability, and increasing changes in the hue and the color tone of hair appearance depending on viewing angle of the hair, and preferably 60° C. or lower, more preferably 50° C. or lower, and further preferably 40° C. or lower from the viewpoint of suppressing skin stimulation.

After the step (II), hair can be rinsed and/or washed. For rinsing, optional aqueous media known in the art, preferably water, more preferably tap water can be used, and for washing, optional washing compositions known in the art, preferably a shampoo composition can be used. The root portion, tip portion and portion between them of hair can be simultaneously or separately rinsed and washed.

After or before the above rinsing or washing, or instead of rinsing or washing, an optional conditioning composition known in the art can be applied to hair.

After the step (II) and the above optional rinsing and/or washing, hair can be optionally dried. Drying tools e.g. towel or an electric drying tool such as a fan dryer can be used to dry hair, and hair can be partially or completely dried.

With respect to the embodiments described above, preferable aspects of the present invention will now be further disclosed.

<1>

A method for treating hair, in which hair is divided into the following A layer and B layer using as a boundary a depth X % in a depth range of 10% or more and 65% or less from the surface of hair toward the center along the long diameter axis extending through the center of the cross-section of hair, and at least one value of color difference ΔE*, hue difference Δh and chroma difference ΔC* between the color of the A layer and the color of the B layer is adjusted to 3 or more to provide visual changes in the hue and the color tone of hair appearance depending on viewing angle of the hair:

A layer: a portion of a continuous color from the surface of hair to the depth X %, and B layer: a portion including the center and having a continuous color different from the A layer, in which the depth from the surface of hair exceeds X %.

<2>

A method for treating hair, in which hair is divided into the following A layer and B layer using as a boundary a depth X % in a depth range of 5% or more and 80% or less from the surface of hair toward the center along the long diameter axis extending through the center of the cross-section of hair, and at least one value of color difference ΔE*, hue difference Δh and chroma difference ΔC* between the color of the A layer and the color of the B layer is adjusted to 8 or more to provide visual changes in the hue and the color tone of hair appearance depending on viewing angle of the hair:

A layer: a portion of a continuous color from the surface of hair to the depth X %, and B layer: a portion including the center and having a continuous color different from the A layer, in which the depth from the surface of hair exceeds X %.

<3>

A method for treating hair, in which hair is divided into the following A layer and B layer using as a boundary a depth X % in a depth range of 5% or more and 80% or less from the surface of hair toward the center along the long diameter axis extending through the center of the cross-section of hair, and at least one value of color difference ΔE*, hue difference Δh and chroma difference ΔC* between the color of the A layer and the color of the B layer is adjusted to 3 or more to provide visual changes in the hue and the color tone of hair appearance depending on viewing angle of the hair, where the color of the B layer is a color dyed using an oxidation dye intermediate, and the color of the A layer is a color dyed using a dye comprising one or more dyes (A) selected from the group consisting of preferably the following (A-1) to (A-8), more preferably (A-1) to (A-4), and further preferably (A-1) to (A-3):

[Chem. 3]

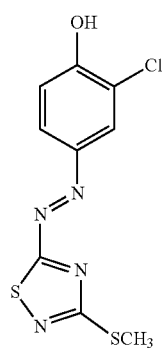

(A-1)

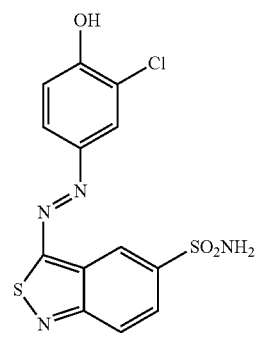

(A-2)

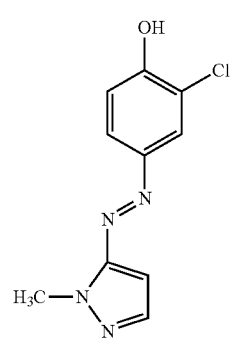

(A-3)

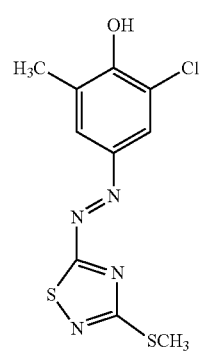

(A-4)

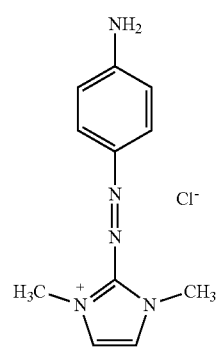

(A-5)

-continued

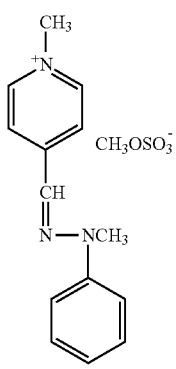
(A-6)

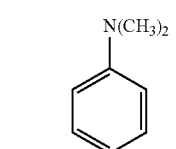
(A-7)

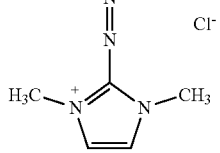
(A-8)

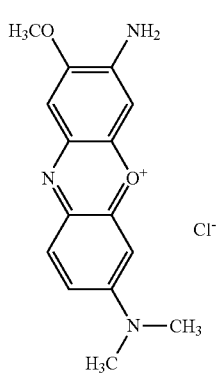

A layer: a portion of a continuous color from the surface of hair to the depth X %, and B layer: a portion including the center and having a continuous color different from the A layer, in which the depth from the surface of hair exceeds X %.

<4>

The method for treating hair according to <2> or <3>, where the depth X % is preferably 7% or more and 75% or less, more preferably 10% or more and 65% or less, further preferably 15% or more and 60% or less, further preferably 17% or more and 55% or less, and further preferably 20% or more and 50% or less.

<5>

The method for treating hair according to any one of <1>, <3> or <4>, where at least one value of color difference $\Delta E^*$, hue difference $\Delta h$ and chroma difference $\Delta C^*$ between the color of the A layer and the color of the B layer is preferably 5 or more, more preferably 8 or more, further preferably 10 or more, further preferably 15 or more, further preferably 20 or more, further preferably 25 or more, and further preferably 30 or more.

<6>

The method for treating hair according to any one of <1> to <5>, where when the angles of a line connecting a light source and hair, and a line connecting hair and observer's eyes, and/or the angles of the surface of hair are changed, at least one of $\Delta E^*_1 - \Delta E^*_0$, $\Delta H_1 - \Delta H_0$ and $\Delta C^*_1 - \Delta C^*_0$, which are differences of $\Delta E^*_0$, $\Delta h_0$ and $\Delta C^*_0$ values between two points with the highest contrast on the surface of hair having only a color in a B layer without an A layer, and $\Delta E^*_1$, $\Delta h_1$ and $\Delta C^*_1$ values between two points with the highest contrast on the surface of hair having an A layer and a B layer, is adjusted to 3 or more, preferably 5 or more, more preferably 8 or more, further preferably 10 or more, further preferably 15 or more, further preferably 20 or more, further preferably 25 or more, and further preferably 30 or more.

<7>

The method for treating hair according to any one of <3> to <6>, where the hair dyeing of the B layer by an oxidation dye intermediate is carried out by a hair dye agent comprising a precursor and a coupler as an oxidation dye intermediate.

<8>

A method for treating hair, in which hair is divided into the following A layer and B layer using as a boundary a depth X % in a depth range of 5% or more and 65% or less from the surface of hair toward the center along the long diameter axis passing through the center of the cross-section of hair, and at least one value of color difference $\Delta E^*$, hue difference $\Delta h$ and chroma difference $\Delta C^*$ between the color of the A layer and the color of the B layer is adjusted to 10 or more to provide visual changes in the hue and the color tone of hair appearance depending on viewing angle of the hair, where the color of the A layer is a color dyed using a dye comprising one or more dyes (A) selected from the group consisting of the following (A-1) to (A-3):

[Chem. 4]

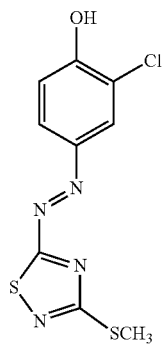
(A-1)

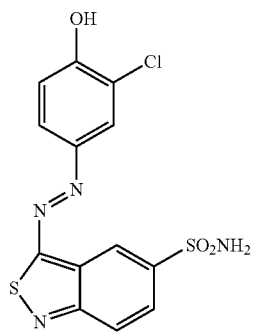
(A-2)

-continued (A-3)

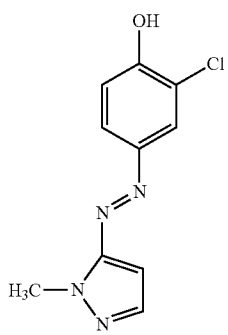

A layer: a portion of a continuous color from the surface of hair to the depth X %, and B layer: a portion including the center and having a continuous color different from the A layer, in which the depth from the surface of hair exceeds X %.

<9>

A method for treating hair, in which hair is divided into the following A layer and B layer using as a boundary a depth X % in a depth range of 5% or more and 65% or less from the surface of hair toward the center along the long diameter axis extending through the center of the cross-section of hair, and at least one value of color difference ΔE*, hue difference Δh and chroma difference ΔC* between the color of the A layer and the color of the B layer is adjusted to 10 or more, where the color of the A layer is a color dyed using a dye comprising one or more dyes (A) selected from the group consisting of the following (A-1) to (A-3), and

[Chem. 5]

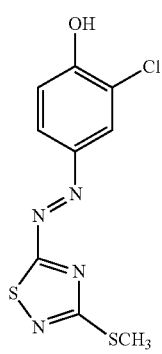

(A-1)

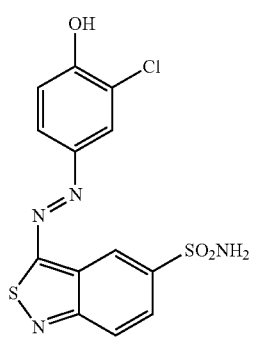

(A-2)

-continued (A-3)

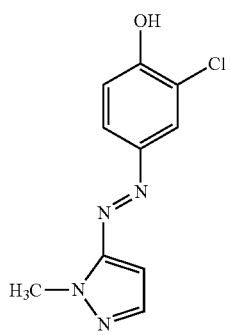

at least one of $\Delta E^*_1 - \Delta E^*_0$, $\Delta h_1 - \Delta h_0$ and $\Delta C^*_1 - \Delta C^*_0$, which are differences of $\Delta E^*_0$, $\Delta h_0$ and $\Delta C^*_0$ values between two points with the highest contrast on the surface of hair having only a color in a B layer without an A layer, and $\Delta E^*_1$, $\Delta h_1$ and $\Delta C^*_1$ values between two points with the highest contrast on the surface of hair having an A layer and a B layer, where the angles of a line connecting a light source and hair, and a line connecting hair and observer's eyes, and/or the angles of the surface of hair are changed is adjusted to 3.3 or more to provide visual changes in the hue and the color tone of hair appearance depending on viewing angle of the hair:

A layer: a portion of a continuous color from the surface of hair to the depth X %, and B layer: a portion including the center and having a continuous color different from the A layer, in which the depth from the surface of hair exceeds X %.

<10>

The method for treating hair according to <9>, where at least one of $\Delta E^*_1 - \Delta E^*_0$, $\Delta h_1 - \Delta h_0$ and $\Delta C^*_1 - \Delta C^*_0$ is adjusted to 8 or more.

<11>

A method for dyeing hair, having the following steps (I) and (II):

Step (I): dyeing or bleaching hair by applying to hair a mixture obtained by mixing a first agent comprising an alkaline agent and a second agent comprising an oxidizing agent, and Step (II): after the step (I), dyeing hair by applying to hair a hair dye agent comprising one or more dyes (A) selected from the group consisting of the following (A-1) to (A-8), preferably the following (A-1) to (A-4), more preferably (A-1) to (A-3).

[Chem. 6]

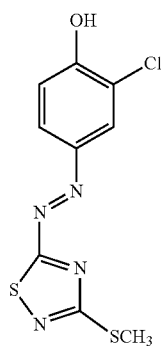

(A-1)

-continued (A-2)
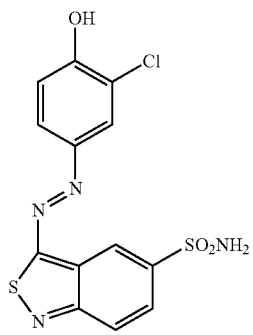

(A-3)
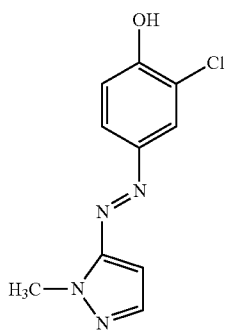

(A-4)
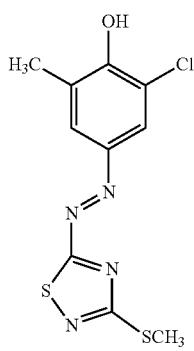

(A-5)
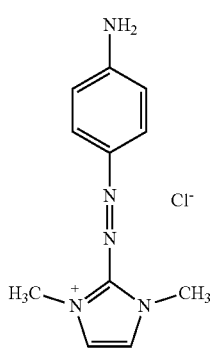

-continued (A-6)
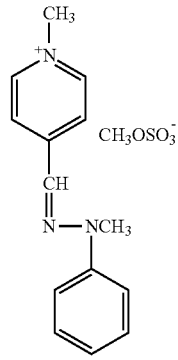

(A-7)
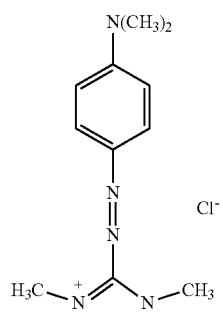

(A-8)
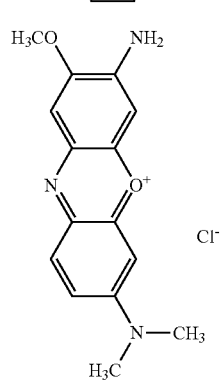

<12>

The method for dyeing hair according to <11>, where the first agent further comprises a precursor as an oxidation dye intermediate.

<13>

The method for dyeing hair according to <11>, where the first agent further comprises a precursor and a coupler as an oxidation dye intermediate.

<14>

A method for dyeing hair, having the following steps (I), (II) and (III):

Step (I): dyeing or bleaching hair by applying to hair a mixture obtained by mixing a first agent comprising an alkaline agent and a second agent comprising an oxidizing agent, Step (II): after the step (I), applying to hair a hair dye agent comprising one or more dyes (A) selected from the group consisting of the following (A-1) to (A-3), and leaving the hair to stand for 10 minutes or longer and 60 minutes or shorter, and

[Chem. 7]

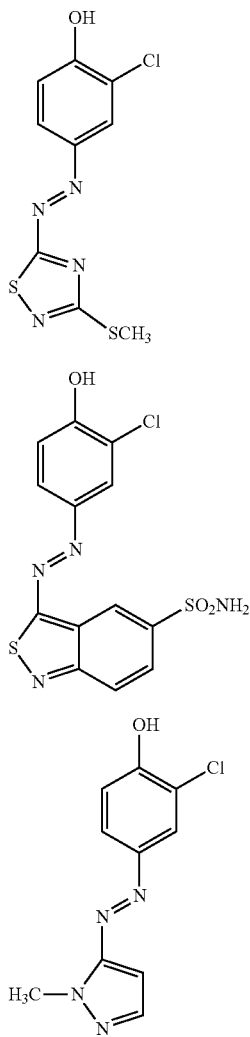

(A-1)

(A-2)

(A-3)

Step (III): after the step (II), rinsing or washing hair.

EXAMPLES

Test Example 1

First agents A to C and F to H shown in Table 1, and a second agent E shown in Table 2 were prepared, and a relationship between hair dyeing conditions and the depth of dye (A) which penetrates hair (depth X %) was investigated.

(Method for Dyeing Hair)

The first agents A to C, each 4 g, and the second agent E, 6 g, were taken, and each of the first agents and the second agent were sufficiently mixed by a stirrer (mixing ratio 1:1.5). The obtained mixed solution was put on a hair dyeing tray, and applied with rubbing to both sides of a hair tress of Caucasian hair (International Hair Importers & Products, Inc., Natural White; 15 cm in length, 1.5 g in weight, the same applies hereinafter) 30 times per side using a brush. In addition, the first agents F to H, 10 g, were taken, and applied to the above Caucasian hair tress in the same manner as above without mixing a second agent. At this time, when A, C, G and H were used as a first agent, the obtained solution was applied to a hair tress, when B was used as a first agent, the obtained solution was applied to three hair tress, and when F was used as a first agent, the obtained solution was applied to 6 hair tress.

After application, a solution adhering to a hair tress was partially removed with hands, and the bath ratio (the mass of hair tress:the mass of solution applied to the hair tress) was adjusted to 1:0.7 in solutions using the first agents A to C, and 1:1 in those using the first agents F to H. After that, the hair tress was left to stand at 30° C. for time shown in Table 3. Subsequently, the hair tress was rinsed with 40° C. hot water for 30 seconds, and treatments of washing with a shampoo for laboratory evaluation→rinsing with the same hot water→treating with a conditioner for laboratory evaluation→rinsing with the same hot water were carried out for 15 seconds each, followed by drying with cold air to prepare a dyed hair tress.

(Method for Measuring Depth X %)

From the dyed hair tress, 5 hairs were taken, and arranged on a SUMP plate (SUMP PLATE manufactured by SUMP LABORATORY TOKYO JAPAN). Acetone was added dropwise thereto and another SUMP plate was put thereon. A weight (1 kg) was put thereon, and hairs were dried for a day. Two sets per sample were created. A hair was cut at a thickness of 20 μm using a microtome (LEICA ultramicrotome Ultracut N manufactured by Hitachi High-Tech Fielding Corporation), and a cross-section was observed by an optical microscope (E800 manufactured by Nikon, magnification: 40-fold, perfume: 12, aperture: DICM, exposure time: 60 to 150 ms) and a laser microscope (VK-8710 manufactured by KEYENCE, 100-fold magnification, zoom 1.0×), and a photograph was taken.

A portion having a continuous color from the periphery of hair toward the center on a taken image was determined as the length of an A layer, and the total length of the A layer from both peripheral parts along the long diameter of hair was measured with a scale, and a depth X was calculated in accordance with the following formula.

Depth $X$ (%)=Total length of $A$ layer/long diameter of hair×100

When the end of an A layer is not clear, the midpoint of the gradation portion was determined as the length of the A layer. In addition, as a method for accurately measuring a midpoint, there is a means in which changes in $L^*a^*b^*$ values or RGB values on a microscope image were monitored along the long diameter axis of hair using an image analysis software (ImageJ: manufactured by National Institutes of health), and in a position in which any value greatly changes, the midpoint of the starting point and the ending point of the change was determined as the boundary surface of an A layer and a B layer. Because the color of a dye largely related to hair dyeing of an A layer is red this time, a method in which changes in $a^*$ values are monitored was used; however, as a result of verification, the obtained results were the almost same as in a method by visual inspection.

Ten hairs per hair tress were measured, and the average value was used as a depth X %. The results of a relationship between time in a hair dyeing treatment and depth X % are shown in Table 3. "Conditions" in Table 3 indicate combinations of the type of used first agent and time.

TABLE 1

| First agent (mass %) | A | B | C | F | G | H |
|---|---|---|---|---|---|---|
| Dye (A-4) | 1.25 | 0.313 | 0.125 | — | — | — |
| Dye (A-1) | — | — | — | 0.12 | — | — |
| Dye (A-2) | — | — | — | — | 0.12 | — |
| Dye (A-3) | — | — | — | — | — | 0.2 |
| EDTA-4Na | 0.10 | 0.10 | 0.10 | 0.05 | 0.05 | 0.05 |
| Decyl glucoside | 18.50 | 18.48 | 18.48 | — | — | — |
| Sodium laureth sulfate | 4.60 | 4.62 | 4.62 | — | — | — |
| Potassium oleate (50 mass %) | 0.40 | 0.40 | 0.40 | — | — | — |
| Propylene glycol | 4.00 | 4.00 | 4.00 | — | — | — |
| (C11-15) Pareth-9 | 0.50 | 0.50 | 0.50 | — | — | — |
| Laureth-23 | 2.00 | 2.00 | 2.00 | — | — | — |
| Myristyl alcohol | 0.20 | 0.20 | 0.20 | — | — | — |
| Monoethanolamine | 0.80 | 0.80 | 0.80 | — | — | — |
| Aqueous ammonia (28 mass %) | 4.00 | 4.00 | 4.00 | — | — | — |
| 2-Amino2-methylpropanol | — | — | — | 4.00 | 4.00 | 4.00 |
| Hydrochloric acid (6 N) | 4.30 | 4.30 | 4.30 | — | — | — |
| Ethanol | 10.50 | 10.52 | 10.52 | — | — | — |
| Water | 48.85 | 49.767 | 49.955 | 95.83 | 95.83 | 95.75 |
| Total | 100.00 | 100.00 | 100.00 | 100.00 | 100.00 | 100.00 |

TABLE 2

| Second agent (mass %) | E | I |
|---|---|---|
| Hydrogen peroxide (50 mass %) | 11.41 | 11.41 |
| Sodium laureth sulfate | 1.06 | — |
| Cetanol | 0.46 | — |
| Stearyl alcohol | 0.12 | — |
| Myristyl alcohol | 0.34 | — |
| Salicylic acid | 0.015 | — |
| 4'-Hydroxyacetanilide | 0.015 | — |
| 8-Quinolinol | — | 0.04 |
| 1-Hydroxyethylidene-1,1-diphosphonic acid (60 mass % aqueous solution) | — | 0.08 |
| Etidronic acid (60 mass %) | 0.13 | — |
| Sodium hydroxide (32 mass %) | 0.01 | — |
| Phosphoric acid | — | 0.465 |
| Water | 86.44 | 88.005 |
| Total | 100.00 | 100.00 |

TABLE 3

| Conditions | First agent | | Second agent | | Temperature | Time | Depth X |
|---|---|---|---|---|---|---|---|
| A-30 | A | 4 g | E | 6 g | 30° C. | 30 min | 9.4% |
| B-15 | B | 4 g | E | 6 g | 30° C. | 15 min | 21% |
| B-30 | B | 4 g | E | 6 g | 30° C. | 30 min | 29% |
| B-60 | B | 4 g | E | 6 g | 30° C. | 60 min | 28% |
| C-30 | C | 4 g | E | 6 g | 30° C. | 30 min | 34% |
| F-0 | F | 10 g | — | — | 30° C. | 0 min | <5% |
| F-5 | F | 10 g | — | — | 30° C. | 5 min | 11% |
| F-45 | F | 10 g | — | — | 30° C. | 45 min | 22% |
| F-90 | F | 10 g | — | — | 30° C. | 90 min | 30% |
| F-240 | F | 10 g | — | — | 30° C. | 4 h | 60% |
| F-1440 | F | 10 g | — | — | 30° C. | 1 day | 100% |
| G-45 | G | 10 g | — | — | 30° C. | 45 min | 6% |
| H-45 | H | 10 g | — | — | 30° C. | 45 min | 17% |

Examples 1 to 8 and Comparative Examples 1 to 6

Step (I) was carried out using a first agent shown in Table 4 and a second agent shown in Table 2 in accordance with the following procedure. After that, Step (II) was further carried out using a first agent shown in Table 1 and a second agent shown in Table 2 in Example 1, and using a first agent shown in Table 1 in Examples 2 to 8 and Comparative Examples 4 and 5. Comparative Examples 1 to 3 and 6 were used as a reference without carrying out the step (II).

Step (I): The type and amount of the first agent and the second agent shown in Table 5 were taken, and they were sufficiently mixed by a stirrer. The obtained mixed solution was put on a hair dyeing tray, and applied with rubbing to both sides of a hair tress of Caucasian hair 30 times each side using a brush. After application, a mixed solution adhering to the hair tress was partially removed with hands, and the bath ratio (the mass of hair tress:the mass of mixed solution applied to the hair tress) was adjusted to a ratio shown in Table 5. The hair tress was left to stand at 30° C. for time shown in Table 5. Subsequently, the hair tress was rinsed with 40° C. hot water for 30 seconds, and treatments of washing with a shampoo for laboratory evaluation→rinsing with the same hot water→treating with a conditioner for laboratory evaluation→rinsing with the same hot water were carried out for 15 seconds each, followed by drying with cold air.

Step (II): Furthermore, in Examples 1 to 8 and Comparative Examples 4 and 5, a hair dyeing treatment was carried out using the type and amount of agent shown in Table 5 in accordance with treatment conditions shown in Table 3.

Evaluation described as follows was made about hair tress dyed in Examples and Comparative Examples.

TABLE 4

| First agent (mass %) | D | J | K | L |
|---|---|---|---|---|
| Toluene-2,5-diamine solution (20 mass %) | 0.76 | 1.00 | 3.00 | — |
| 2,4-Diaminophenoxyethanol hydrochloride | 0.21 | 0.40 | 1.20 | — |
| p-aminophenol | — | — | — | 0.896 |
| Resorcinol | — | — | — | 0.88 |
| 5-Amino-o-cresol | — | — | — | 0.099 |
| EDTA-4Na | 0.10 | 0.1 | 0.1 | 0.1 |
| Decyl glucoside | 18.50 | — | — | — |
| Sodium laureth sulfate | 4.60 | — | — | — |
| Potassium oleate (50 mass %) | 0.40 | — | — | — |
| Propylene glycol | 4.00 | — | — | — |
| (C11-15) Pareth-9 | 0.50 | — | — | — |
| Laureth-23 | 2.00 | — | — | — |
| Myristyl alcohol | 0.20 | — | — | — |
| Sodium sulfite | — | 0.46 | 0.38 | 0.48 |
| Ascorbic acid | — | 0.4 | 0.4 | 0.4 |
| Monoethanolamine | 0.80 | 6 | 6 | 6 |
| Aqueous ammonia (28 mass %) | 4.00 | 3 | 3 | 3 |
| Ammonium chloride | — | 0.86 | 0.86 | 0.86 |
| Hydrochloric acid (6N) | 4.30 | — | — | — |
| Ethanol | 10.50 | — | — | — |
| Water | 49.13 | 87.78 | 85.06 | 87.285 |
| Total | 100.00 | 100.00 | 100.00 | 100.00 |

(Method for Measuring Color Difference Between A Layer and B Layer)

Method for measuring the color of an A layer: in Examples 2 to 8 and Comparative Example 5, after the step (I) and step (II), different 6 points on the surface of hair (each one point in the central part of the front and back of each region obtained by dividing a hair tress into 3 portions in the length direction) were measured using a chroma meter CR-400 manufactured by KONICA MINOLTA, Inc., and each average value of $L^*$, $a^*$, $b^*$, $C^*$ and h values was used as the color of an A layer.

Method for measuring the color of a B layer: in Comparative Examples 2, 3 and 6, after the step (I), different 6 points on the surface of hair (each one point in the central part of the front and back of each region obtained by dividing a hair tress into 3 portions in the length direction) were measured using a chromo meter CR-400 manufactured by KONICA MINOLTA, Inc., and each average value of $L^*$, $a^*$, $b^*$, $C^*$ and h values was used as the color of a B layer.

The $\Delta E^*$ value of each layer was calculated in accordance with the following formula, and as $\Delta h$ and $\Delta C^*$, respective differences were calculated.

$$\Delta E^* = \sqrt{(L^*_1 - L^*_0)^2 + (a^*_1 - a^*_0)^2 + (b^*_1 - b^*_0)^2}$$ [Math.1]

(Evaluation Method 1 for Changes in Hue and Color Tone of Hair Appearance Depending on Viewing Angle of the Hair)

It is believed that the effect of changing the hue and the color tone of hair appearance depending on viewing angle of the hair is expressed by affecting elements of various observing conditions each other, and it is believed that sensory evaluation by evaluators grasps an actual state. Therefore, evaluation was made by the following method.

When a hair tress was held with hands just under a fluorescent light fixed on the ceiling and the hair tress was held horizontally and in the longitudinal direction to an evaluator, a position was taken such that observer's eyes are at 45° to the surface of the hair tress. With the state maintained, angles were changed from horizon to vertical without moving the position of the hair tress, and changes in hue, color tone, and contrast during that were observed, and the effect of showing different colors depending on viewing angle was evaluated. A sensory evaluation was carried out by 3 trained panelists in accordance with criterion described below, and the average of evaluation by three panelists was obtained (rounded off to one decimal place). The results are shown in Table 5 (shown using $\Delta E^*$ as a representative value). $\Delta h$ is 2.2 and $\Delta C^*$ is 0.5 in Comparative Example 5.

(Evaluation Criterion)

1: changes in color were not observed,

2: changes in color were observed, and

3: great changes in color were observed.

(Evaluation Method 2 for Changes in Hue and the Color Tone of Hair Appearance Depending on Viewing Angle of the Hair)

The "changes in hue and the color tone of hair appearance depending on viewing angle of the hair" can be evaluated in a sensory manner by the evaluation method 1; however, evaluation was also made by a method using measurement described below.

A hair tress to be measured was fixed along the curve of a cylindrical stand with a cross-section radius of 5.5 cm. This hair tress was put under a light source at a distance of 2 to 3 m, and photographs were taken at a distance of 1 m from the hair tress while changing various angles in the circumferential direction and the axis direction of the cylindrical stand. At this time, a position in which two highlighted regions (strip-shaped regions which are generated by mirror reflection of light from a light source and appear bright) appear apart from each other was found to take photographs. As the light source, Life look HGX 3-band fluorescent lamp Daylight (FHF32EX-N-HX-S) manufactured by NEC was used. As a camera, NIKON D90 was used, the aperture value was f/5.6, the exposure time was 1/10 sec, the ISO speed was ISO-400, and a photograph of a color patch (Kodak Color Separation Guide and Gray Scale Q-14) was taken at the same time.

All taken images were printed out, and in a region between the above two highlighted regions on the images, the color difference ($\Delta E^*$), hue difference ($\Delta h$) and chroma difference ($\Delta C^*$) between two strip-shaped regions in which e.g., brightness, hue and chroma are most different were measured by a color-difference meter, and the greatest $\Delta E^*$, $\Delta h$ and $\Delta C^*$ were identified. Images were printed out on paper (G80A4W) manufactured by Mitsubishi Paper Mills Limited using a printer manufactured by Canon Inc., Canon Image RUNNER ADVANCE (iR-ADVC5255F), and colors were measured using a chroma meter CR-400 manufactured by KONICA MINOLTA, Inc. Using as references Comparative Example 1 for Example 1, Comparative Examples 2 for Examples 2 and 8, Comparative Example 3 for Examples 3 to 6 and Comparative Examples 4 and 5, and Comparative Example 6 for Example 7, the above differences of color difference ($\Delta E^*$), hue difference ($\Delta h$) and chroma difference ($\Delta C^*$), i.e. A ($\Delta E^*$)=$\Delta E^*$ (target hair)-$\Delta E^*$ (reference), A ($\Delta h$)=$\Delta h$ (target hair)-$\Delta h$ (reference), and A ($\Delta C^*$)=$\Delta C^*$ (target hair)-$\Delta C^*$ (reference) were evaluated.

The greatest ones of A ($\Delta E^*$), A ($\Delta h$) and A ($\Delta C^*$) are shown in Table 5.

TABLE 5

| | | | Examples | | | | | | | |
|---|---|---|---|---|---|---|---|---|---|---|
| | | | 1 | 2 | 3 | 4 | 5 | 6 | 7 | 8 |
| Step (I) (hair dyeing of inner layer (B layer)) | First agent (Table 4) | | D 4 g | J 4 g | K 4 g | K 4 g | K 4 g | K 4 g | L 5 g | J 4 g |
| | Second agent (Table 2) | | E 6 g | I 6 g | I 6 g | I 6 g | I 6 g | I 6 g | I 10 g | I 6 g |
| | Bath ratio (hair tress:mixed solution) | | 1:0.7 | 1:1 | 1:1 | 1:1 | 1:1 | 1:1 | 1:1 | 1:1 |
| | Time (min) | | 15 | 30 | 30 | 30 | 30 | 30 | 30 | 30 |
| Step (II) (hair dyeing of outer layer (A layer)) | First agent (Table 1) | | B 4 g | F 10 g | F 10 g | F 10 g | F 10 g | F 10 g | G 10 g | H 10 g |
| | Second agent (Table 2) | | E 6 g | — | — | — | — | — | — | — |
| | Bath ratio (hair tress:mixed solution) | | 1:0.7 | 1:1 | 1:1 | 1:1 | 1:1 | 1:1 | 1:1 | 1:1 |
| | Treatment conditions (Table 3) | | B-30 | F-5 | F-5 | F-45 | F-90 | F-240 | G-45 | H-45 |
| Constitution of color in hair | Outer layer in hair (A layer) | Color | Red | Red | Red | Red | Red | Red | Blue | — |
| | | Depth X (%) | 29 | 11 | 11 | 22 | 30 | 60 | 6 | — |
| | Inner layer in hair (B layer) | Color | Blue | Blue | Blue | Blue | Blue | Blue | Brown | Blue |
| | Color difference (ΔE*) of A layer and B layer | | over 3 | 10.7 | 3.2 | 12.9 | 14.9 | 14.9 | 19.2 | 20.1 |
| Evaluation | Changes in hue and color tone depending on viewing angle of the hair (Evaluation method 1) | | 3.0 | 2.7 | 2.0 | 3.0 | 3.0 | 2.7 | 2.7 | 2.7 |
| | Changes in hue and color tone depending on viewing angle of the hair (Evaluation method 2) | | Δ(ΔE*) 8.4 | Δ(ΔE*) 3.9 | Δ(Δh) 3.2 | Δ(ΔC*) 3.4 | Δ(Δh) 10.5 | Δ(ΔC*) 5.9 | Δ(ΔE*) 7.6 | Δ(ΔE*) 3.7 |

| | | | Comparative Examples | | | | | |
|---|---|---|---|---|---|---|---|---|
| | | | 1 | 2 | 3 | 4 | 5 | 6 |
| Step (I) (hair dyeing of inner layer (B layer)) | First agent (Table 4) | | D 4 g | J 4 g | K 4 g | K 4 g | K 4 g | L 5 g |
| | Second agent (Table 2) | | E 6 g | I 6 g | I 6 g | I 6 g | I 6 g | I 10 g |
| | Bath ratio (hair tress:mixed solution) | | 1:0.7 | 1:1 | 1:1 | 1:1 | 1:1 | 1:1 |
| | Time (min) | | 15 | 30 | 30 | 30 | 30 | 30 |
| Step (II) (hair dyeing of outer layer (A layer)) | First agent (Table 1) | | — | — | — | F 10 g | F 10 g | — |
| | Second agent (Table 2) | | — | — | — | — | — | — |
| | Bath ratio (hair tress:mixed solution) | | — | — | — | 1:1 | 1:1 | — |
| | Treatment conditions (Table 3) | | — | — | — | F-1440 | F-0 | — |
| Constitution of color in hair | Outer layer in hair (A layer) | Color | — | — | — | Red | Red | — |
| | | Depth X (%) | — | — | — | 100 | <5 | — |
| | Inner layer in hair (B layer) | Color | Blue | Blue | Blue | Blue | Blue | Brown |
| | Color difference (ΔE*) of A layer and B layer | | — | — | — | *1 | 1.3 | — |
| Evaluation | Changes in hue and color tone depending on viewing angle of the hair (Evaluation method 1) | | 1.3 | 1.7 | 1.0 | 1.3 | 1.3 | 1.0 |
| | Changes in hue and color tone depending on viewing angle of the hair (Evaluation method 2) | | *2 | *2 | *2 | Δ(ΔE*) 2.4 | Δ(ΔC*) 1.6 | *2 |

*1: not measured because B layer (a portion of a continuous color different from A layer) is totally replaced with A layer and does not exist.
*2: reference

The invention claimed is:

1. A method for treating hair, comprising:
treating hair such that the hair is divided into A layer and B layer with a boundary at a depth X % of 5% or more and 80% or less from the surface of the hair toward the center of a cross-section of the hair along the long diameter axis extending through the center of the cross-section of the hair, and that at least one value of color difference ΔE*, hue difference Δh and chroma difference ΔC* between a color of the A layer and a color of the B layer is adjusted to 3 or more to provide visual changes in the hue and the color tone of hair appearance depending on viewing angle of the hair, wherein
the A layer is a portion having a continuous color from the surface of the hair to the depth X % of the hair,
the B layer is a portion including the center of the hair and having a continuous color different from the color of the A layer, a depth of the B layer from the surface of the hair exceeding X %, the color of the A layer is a color dyed by using a dye comprising at least one dye (A) selected from the group consisting of the following (A-1) to (A-8):
(A-1)
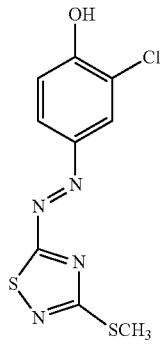
(A-2)
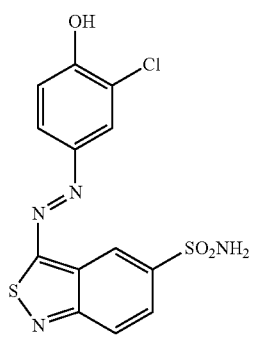
(A-3)
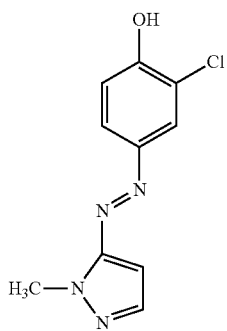
(A-4)
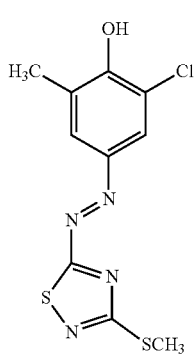
(A-5)
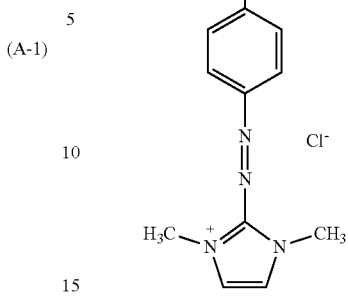
(A-6)
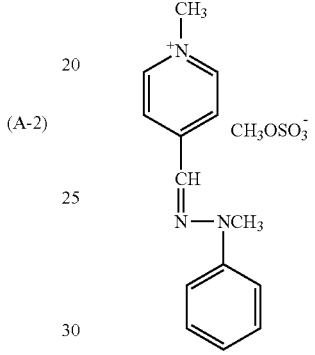
(A-7)
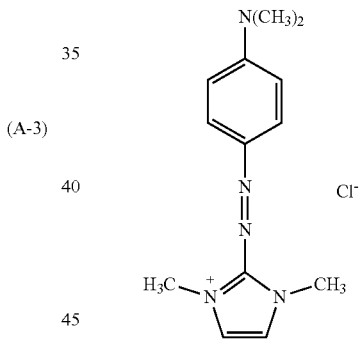
(A-8)
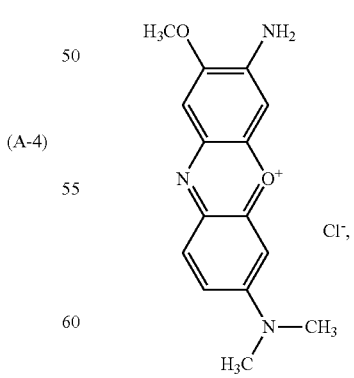
and
the color of the B layer is a color dyed by using a bleach or an oxidation dye intermediate.

2. A method for dyeing hair, comprising:
(I): dyeing or bleaching hair by applying to the hair a mixture obtained by mixing a first agent comprising an alkaline agent and a second agent comprising an oxidizing agent; and subsequently
(II): dyeing the hair by applying to the hair a hair dye agent comprising at least one dye (A) selected from the group consisting of the following (A-1) to (A-8):

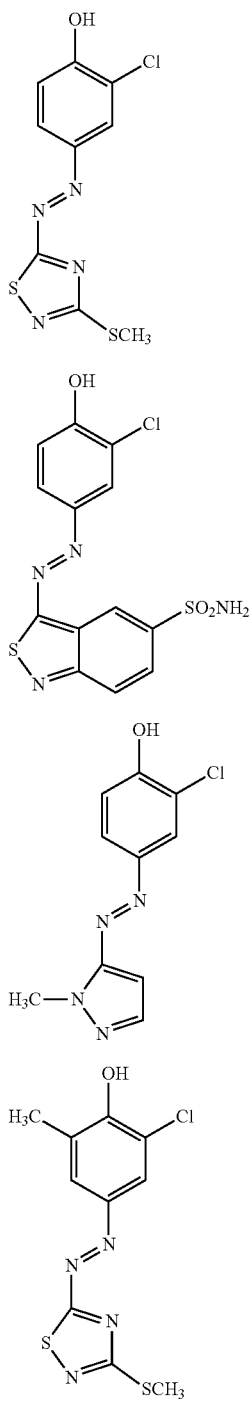

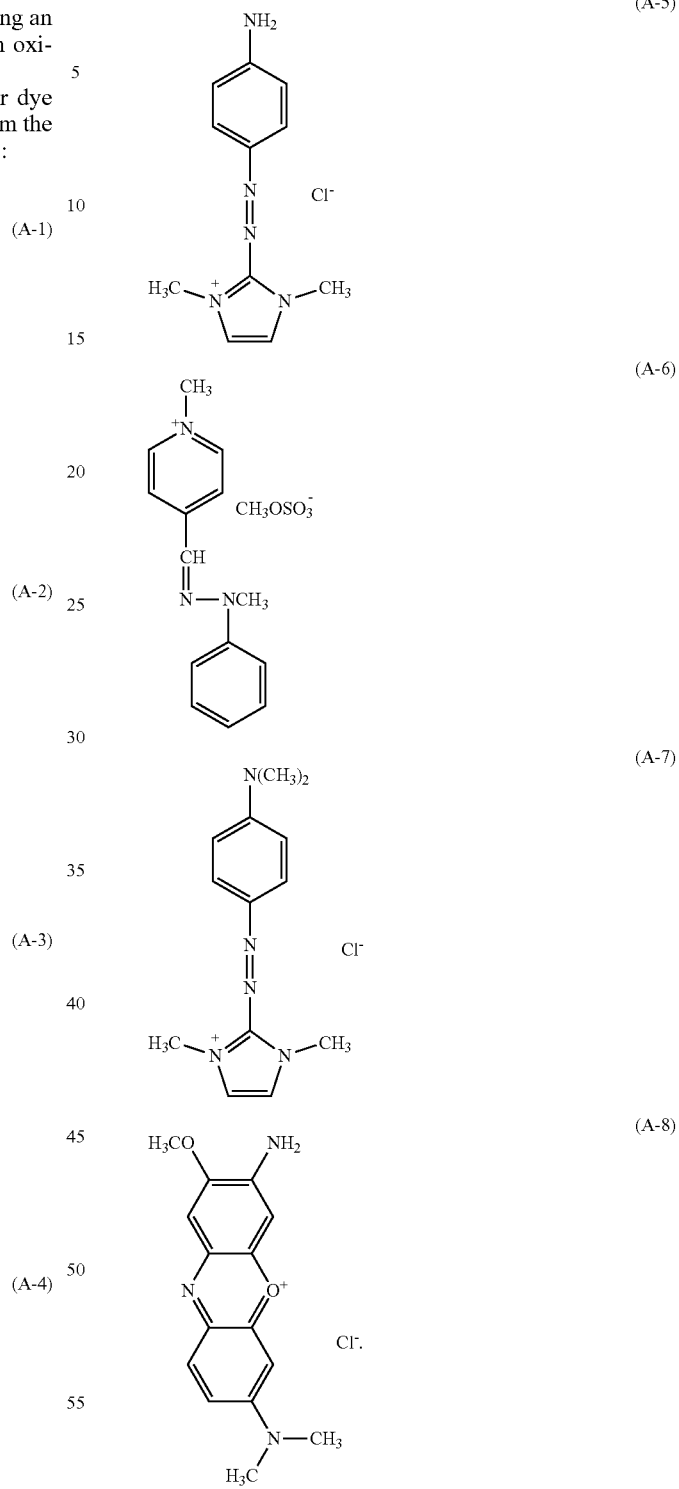

3. The method according to claim 2, wherein the first agent used in (I) further comprises an oxidation dye intermediate.

* * * * *